(12) United States Patent
Klemm

(10) Patent No.: US 11,517,224 B2
(45) Date of Patent: Dec. 6, 2022

(54) IMPLANTABLE GLUCOSE MONITOR

(71) Applicant: SANOFI, Paris (FR)

(72) Inventor: Thomas Klemm, Frankfurt am Main (DE)

(73) Assignee: Sanofi, Paris (FR)

( * ) Notice: Subject to any disclaimer, the term of this patent is extended or adjusted under 35 U.S.C. 154(b) by 228 days.

(21) Appl. No.: 16/765,236

(22) PCT Filed: Nov. 15, 2018

(86) PCT No.: PCT/EP2018/081304
§ 371 (c)(1),
(2) Date: May 19, 2020

(87) PCT Pub. No.: WO2019/101612
PCT Pub. Date: May 31, 2019

(65) Prior Publication Data
US 2020/0275867 A1    Sep. 3, 2020

(30) Foreign Application Priority Data

Nov. 21, 2017 (EP) ..................................... 17306607

(51) Int. Cl.
*A61B 5/1455* (2006.01)
*A61B 5/145* (2006.01)
(Continued)

(52) U.S. Cl.
CPC .......... *A61B 5/14532* (2013.01); *A61B 5/076* (2013.01); *A61B 5/1459* (2013.01);
(Continued)

(58) Field of Classification Search
CPC ... A61B 5/1455; A61B 5/14532; A61B 5/076; A61B 5/14558; A61B 5/1459; A61B 5/6879

See application file for complete search history.

(56) References Cited

U.S. PATENT DOCUMENTS

| 4,704,029 A | 11/1987 | Van Heuvelen |
| 6,246,893 B1 | 6/2001 | Gobeli |

(Continued)

FOREIGN PATENT DOCUMENTS

| CN | 101669825 | 3/2010 |
| DE | 102012014553 | 1/2014 |

(Continued)

OTHER PUBLICATIONS

PCT International Search Report and Written Opinion in Application No. PCT/EP2018/081304, dated Jan. 7, 2019, 11 pages.

(Continued)

*Primary Examiner* — Marjan Fardanesh
(74) *Attorney, Agent, or Firm* — Fish & Richardson P.C.

(57) ABSTRACT

Implantable device for measuring the glucose concentration of a body fluid when implanted, the implantable device comprising a glucose measurement unit, the glucose measurement unit comprising a first light source configured to emit light towards a light transmissive part of a housing of the device and a first optical sensor configured to detect light returned through the light transmissive part from the first light source, and output a first electrical signal based on the detected light; and a wireless communication module configured to wirelessly communicate with an external wireless communication device, wherein the wireless communication module is configured to wirelessly transmit a signal based on the first electrical signal to the external wireless communication device.

16 Claims, 7 Drawing Sheets

(51) Int. Cl.
    *A61B 5/07*         (2006.01)
    *A61B 5/1459*     (2006.01)
    *A61B 5/00*         (2006.01)

(52) U.S. Cl.
    CPC ........ *A61B 5/14558* (2013.01); *A61B 5/6876* (2013.01); *A61B 2560/0219* (2013.01); *A61B 2560/0252* (2013.01)

(56) References Cited

U.S. PATENT DOCUMENTS

| | | |
|---|---|---|
| 2002/0016535 A1 | 2/2002 | Martin et al. |
| 2004/0011671 A1 | 1/2004 | Shults et al. |
| 2010/0160749 A1 | 6/2010 | Gross et al. |

FOREIGN PATENT DOCUMENTS

| | | |
|---|---|---|
| JP | 2013-509944 | 3/2013 |
| JP | 2013-126509 | 6/2013 |
| JP | 2016-502420 | 1/2016 |
| WO | WO 2015/084269 | 6/2015 |

OTHER PUBLICATIONS

PCT International Preliminary Report on Patentability in Application No. PCT/EP2018/081304, dated May 26, 2020, 8 pages.

IMPLANTABLE GLUCOSE MONITOR

CROSS REFERENCE TO RELATED APPLICATIONS

The present application is the national stage entry of International Patent Application No. PCT/EP2018/081304, filed on Nov. 15, 2018, and claims priority to Application No. EP 17306607.7, filed on Nov. 21, 2017, the disclosures of which are incorporated herein by reference.

TECHNICAL FIELD

The present disclosure relates to an implantable device for measuring the glucose concentration of a body fluid when implanted, a system comprising an implantable device, and a method for measuring glucose concentration.

BACKGROUND

Insulin therapy often generally requires repeated blood glucose measurements to be taken from a diabetic patient. Diabetics with Type I diabetes may measure blood glucose 5-9 times a day, while those with gestational diabetes may take measurements up to 11 times per day.

Known blood glucose testing methods involve collecting a blood sample from a patient using a lancet. Blood collection using a lancet may be painful and unpleasant for a diabetic, particularly if a high testing frequency is required. Repeated blood collection from a skin site may lead to the formation of scars or calluses, or increased nerve density, which in turn can make it difficult to collect blood.

SUMMARY

According to an aspect of the present disclosure, there is provided an implantable device for measuring the glucose concentration of a body fluid when implanted, the implantable device comprising: a glucose measurement unit comprising: a first linearly polarized light source configured to emit linearly polarized light to outside of a housing of the device; and a linearly polarized light sensor configured to detect linearly polarized light returned from the linearly polarized light source via the outside of the housing, and output a first electrical signal based on the detected linearly polarized light; and a wireless communication module configured to wirelessly communicate with an external wireless communication device; wherein the wireless communication module is configured to wirelessly transmit a signal based on the first electrical signal to the external wireless communication device. The implantable device allows for continuous remote monitoring of glucose levels within a patient into which the device is implanted, without the need for collecting blood samples using a lancet or similar device.

The linearly polarized light sensor may comprise a linearly polarized light filter and a first optical sensor, wherein the linearly polarized light filter is configured to linearly polarize the light returned through the light transmissive part from the first linearly polarized light source, and wherein the first optical sensor is configured to output the first electrical signal based on the detected light linearly polarized by the linearly polarized light filter.

A plane of polarization of the linearly polarized light filter may be adjustable relative to a plane of polarization of the first linearly polarized light source. This provides an effective means of measuring the angle of optical rotation of linearly polarized light as it passes through a body fluid containing glucose, between the first linearly polarized light source and linearly polarized light filter.

The linearly polarized light filter may comprise a Kerr cell arranged such that the linearly polarized light returned from the linearly polarized light source via the outside of the housing passes through the Kerr cell before being detected by the first optical sensor. This is a simple means of providing a linearly polarized light filter with an adjustable plane of polarization.

The Kerr cell may comprise a first electrode and a second electrode, wherein the glucose measurement unit is configured to apply a potential difference between the first electrode and the second electrode to generate an electric field between the first electrode and second electrode, and wherein the linearly polarized light returned from the linearly polarized light source via the outside of the housing passes through the first electrode and the second electrode, along a path substantially parallel to the electric field. This provides a particularly compact Kerr cell.

The glucose measurement unit may further comprise a second optical sensor and a linear polarizer, wherein the linear polarizer is arranged to linearly polarize light returned from the linearly polarized light source via the outside of the housing, wherein the second optical sensor is arranged to detect the light linearly polarized by the linear polarizer and output a second electrical signal based on the detected light linearly polarized by the linear polarizer, and wherein the wireless communication module is configured to wirelessly transmit the signal based on the second electrical signal. This arrangement provides a simple means for determining the glucose concentration in a body fluid, with improved interference suppression.

The glucose measurement unit may further comprise a second linearly polarized light source, a second optical sensor and a linear polarizer, wherein the second linearly polarized light source is configured to emit linearly polarized light to the outside of the housing, wherein the linear polarizer is arranged to linearly polarize light returned from the second linearly polarized light source via the outside of the housing, wherein the second optical sensor is arranged to detect the light linearly polarized by the linear polarizer and output a second electrical signal based on the detected light linearly polarized by the linear polarizer, and wherein the wireless communication module is configured to wirelessly transmit the signal based on the second electrical signal. This arrangement provides a simple means for determining the glucose concentration in a body fluid, with improved interference suppression.

The wireless communication module may be configured to wirelessly receive power from the external wireless communication device. This is advantageous in that it provides an implantable device that does not require replacement of an internal power source such as a non-rechargeable battery. The implantable device may therefore be repeatedly used to monitor glucose levels over a long period of time without the need to replace the device due to a run-down battery. In some examples, the device may comprise a rechargeable power source such as a battery, wherein the power source is recharged by the power received by the wireless communication module.

The implantable device may be dimensioned to be implantable into a human blood vessel, or tissue well perfused by a body fluid such as blood. This is advantageous since it allows for an accurate measurement of the patient's blood glucose.

The housing of the implantable device may comprise a recess, wherein the light emitted by the first linearly polarized light source to the outside of the housing is emitted through a first side wall of the recess, and wherein the linearly polarized light detected by the linearly polarized light sensor is returned through a second side wall of the recess. This is advantageous in that it provides a simple and effective means of determining the glucose concentration in a body fluid within the recess. The recess may be formed from one or more protrusions of the housing.

The implantable device may further comprise at least one lens arranged to focus the light emitted from the first linearly polarized light source towards a point outside the housing. This allows for accurate measurement of glucose concentration within the body fluid surrounding the housing, while reducing interference from external light sources such as ambient light.

The implantable device may further comprise a temperature sensor, wherein the wireless communication module is configured to wirelessly transmit a signal based on a temperature measured by the temperature sensor to the external wireless communication device. This arrangement allows for temperature effects to be easily taken into account when processing the output of the glucose monitoring unit to determine a glucose concentration, thus providing a more accurate value of glucose concentration.

According to another aspect of the present disclosure, there is provided a system comprising an aforementioned implantable device and an external wireless communication device, wherein the wireless communication module of the implantable device is configured to wirelessly transmit the signal based on the first electrical signal to the external wireless communication device. The system allows for simple and unobtrusive measurements of glucose concentration in a body fluid.

The external wireless communication device may be a smartphone. This is a particularly simple means for wirelessly communicating with the implantable device According to another aspect of the present disclosure, there is provided a method comprising: emitting linearly polarized light, by a first linearly polarized light source of an implantable device, to outside of a housing of the implantable device; detecting, by a linearly polarized light sensor of the implantable device, linearly polarized light returned from the first linearly polarized light source via the outside of the housing; outputting, by the linearly polarized light sensor, a first electrical signal based on the detected linearly polarized light; and wirelessly transmitting, by a wireless communication module of the implantable device, a signal based on the first electrical signal to an external wireless communication device. This method allows for simple and unobtrusive measurements of glucose concentration in a body fluid.

These as well as other advantages of various aspects of the present disclosure will become apparent from the embodiments described hereinafter.

BRIEF DESCRIPTION OF THE FIGURES

Exemplary embodiments of the present disclosure are described with reference to the accompanying drawings, in which.

Reference will now be made in detail to the embodiments of the present disclosure, examples of which are illustrated in the accompanying drawings, wherein like reference numerals refer to like elements throughout.

DETAILED DESCRIPTION

An implantable device for measuring the glucose concentration of a body fluid when implanted is provided. A system comprising the implantable device and an external wireless communication device, and a method of measuring the glucose concentration of a body fluid using the implantable device and external wireless communication device are also provided.

The aforementioned body fluid is a fluid within a human or animal that contains glucose, wherein the glucose concentration can be measured for insulin therapy. The body fluid is preferably blood, but may alternatively or additionally be interstitial fluid. It is preferable to measure the glucose concentration in the blood of a human or animal rather than the interstitial fluid because blood is generally more responsive to changes in glucose concentration than interstitial fluid.

FIG. 1 shows an implantable device 1 in accordance with some aspects of the present disclosure. The implantable device 1 has a housing 10, wherein some or all of the other components of the implantable device 1 are located inside the housing 10.

Figure 1A:
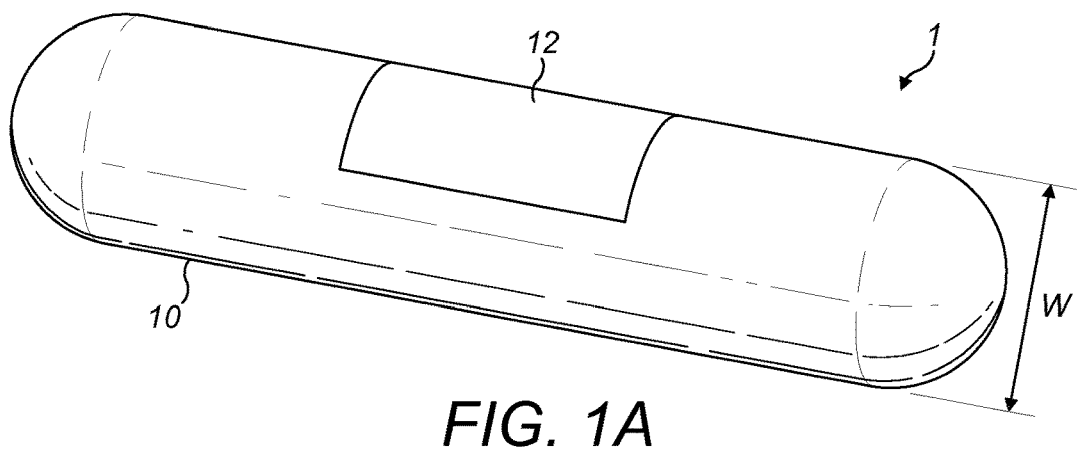
FIG. 1A is a front view of an implantable device according to embodiments of the present disclosure.

The housing 10 has a light transmissive part 12 which allows light of one or more wavelengths to pass through from one side of the light transmissive part 12 to another side. Light is therefore able to pass from outside the housing 10 to the inside of the housing 10 via the light transmissive part 12, and vice versa. A discrete region or window of the housing 10 may comprise the light transmissive part 12, as shown in FIG. 1A. Alternatively, the entire housing 10 may be light transmissive. In some examples, the light transmissive part 12 comprises a plurality of discrete regions of the housing 10, the discrete regions being separated by optically opaque parts of the housing 10.

The housing 10 is preferably made of a biocompatible material such as glass so that the implantable device 1 may be safely implanted into a human or animal. The use of glass for the housing 10 is advantageous in that glass is light transmissive, and hence the housing 10 and light transmissive part 12 may be formed from the same material, in a single manufacturing process.

The implantable device 1 is to be subcutaneously implanted within a human or animal body. Preferably the implantable device 1 can be implanted within a blood vessel of the human or animal, allowing for measurement of the glucose concentration in the blood of said human or animal. In this case, the particular body fluid being measured will be blood.

In some embodiments the implantable device 1 is dimensioned to be implantable into a human blood vessel, such as an artery or vein. For example, the device may have a maximum width w along one axis of around less than 5 mm, preferably around less than 3 mm, and more preferably around 1.35 mm to 2 mm.

In some examples, the implantable device 1 is configured to be implanted into tissue well perfused by a body fluid, such as blood or interstitial fluid. For example, the implantable device 1 may be implanted within the interstitial fluid of a human or animal, for example just under the skin. In this case, the particular body fluid being measured is the interstitial fluid.

Once the implantable device 1 has been implanted, body fluid will surround at least part of the implantable device 1 and come into contact with the light transmissive part 12 of the housing 10. When the implantable device 1 has been implanted in a blood vessel, blood will contact the light transmissive part 12. When the implantable device 1 has been implanted in interstitial fluid, interstitial fluid will be contacting the light transmissive part 12.

Figure 1B:
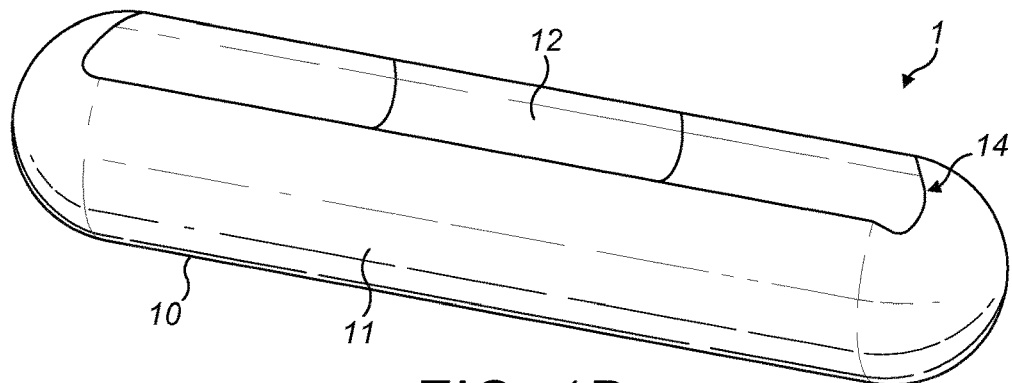
FIG. 1B is a front view of an implantable device having a recess according to embodiments of the present disclosure.

FIG. 1B shows an implantable device 1 similar to the implantable device 1 of FIG. 1A, however the housing 10 of the implantable device shown in FIG. 1B additionally comprises a recess 14, generally formed in an outer surface 11 of the housing 10.

Figure 1C:
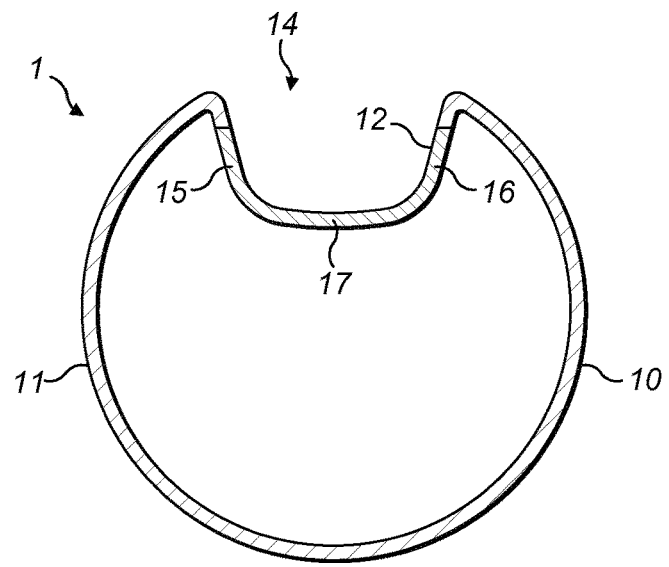
FIG. 1C is a schematic side-view cross-section of the implantable device of FIG. 1B.

FIG. 1C shows a side-view of the implantable device of FIG. 1B, showing a side-view of the recess 14.

As shown in FIG. 1C, the recess 14 may comprise a first side wall 15, a second side wall 16, and a bottom surface 17 adjacent the first side wall 15 and second side wall 16.

The recess 14 may be a groove in the outer surface 11 of the housing. In other embodiments, the recess 14 may be a conduit or tube through which body fluid may flow from one side of the implantable device 1 to another side of the implantable device 1. For example, the conduit or tube may extend from one side of the housing 10 to an opposing side of the housing 10. The recess 14 may be at least partially filled with body fluid when the implantable device 1 is implanted.

Providing a recess 14 in the housing 10 can facilitate the movement of body fluid around the implantable device 1 when the device is implanted. This may be particularly advantageous if the implantable device 1 is implanted into a blood vessel, since the recess may allow blood to flow more easily around or through the implantable device 1. As such, blood flow through the blood vessel is less obstructed by the implanted device 1.

In some examples, the outer surface 11 of the housing 10 may comprise one or more protrusions (not shown) arranged on the outer surface 11. The one or more protrusions may be configured to hold the implantable device 1 in a fixed location within a human or animal body once implanted into said body. If the implantable device 1 is implanted into a blood vessel, the one or more protrusions may be configured to hold the implantable device 1 in a fixed location within the blood vessel by exerting pressure on the inner walls of the blood vessel.

The light transmissive part 12 shown in FIGS. 1B and 1C is comprised in a discrete region of the housing 10, in this case entirely within recess 14. However, the light transmissive part 12 is not limited to this arrangement and may be located in another part of the housing 10, or may comprise the entirety of housing 10.

Figure 2:
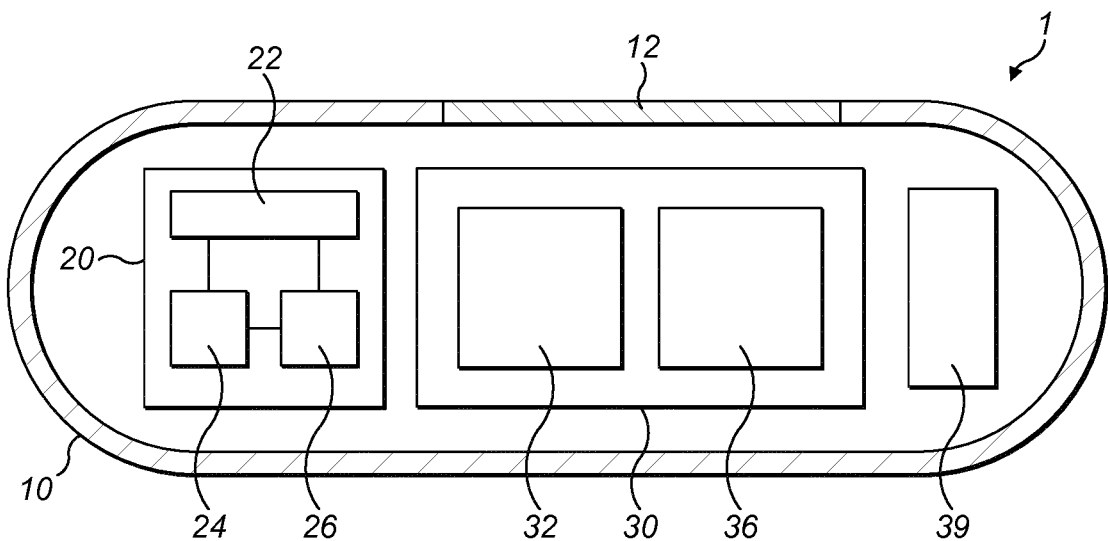
FIG. 2 is a schematic cross-section of an implantable device according to embodiments of the present disclosure.

FIG. 2 is a schematic cross-section of an implantable device 1 according to embodiments of the present disclosure.

The implantable device 1 comprises a wireless communication module 20, a glucose measuring unit 30, and a housing 10 having light transmissive part 12.

Figure 12:
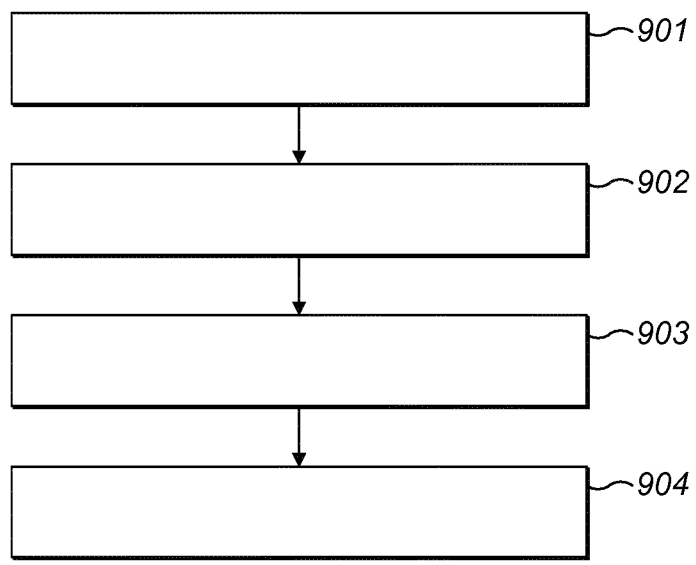
FIG. 12 is a flowchart illustrating a method for determining glucose concentration in a body fluid according to aspects of the present disclosure.

The wireless communication unit 20 is configured to wirelessly communicate with an external wireless communication device 2 (as shown in FIG. 12), preferably using near field communication (NFC), although other wireless protocols and systems may be used.

The wireless communication module 20 is preferably configured to wirelessly receive power from the external wireless communication 2 device by electromagnetic induction.

The wireless communication module 20 comprises an antenna 22, an energy storage unit 24 such as a capacitor or (rechargeable) battery, and a control unit 26 such as an integrated circuit. The antenna 22 is configured to transmit and receive wireless signals, wherein transmission of wireless signals by the antenna is controlled by the control unit 26. The energy storage unit 24 stores electrical energy received from the external wireless communication device 2 via the antenna 22. The control unit 26 may comprise a memory unit (not shown) for storing instructions to be carried out by the control unit 26, and/or data related to measurements made by the glucose measurement unit 30. The control unit 26 may control one or more operations of the glucose measurement unit 30 described herein, and may carry out any of the method steps described herein with respect to the implantable device 1.

The glucose measurement unit 30 comprises a linearly polarized light source 32 and a linearly polarized light sensor 36. The linearly polarized light source 32 may comprise one or more light sources 33 (not shown) such as one or more light emitting diodes (LEDs), and is configured to emit linearly polarized light to an outside of the housing 10. If the linearly polarized light source 30 is located within an inside of the housing 10, the linearly polarized light source 30 may be configured to emit linearly polarized light towards and through the light transmissive part 12 of the housing 10, that is, from the inside of the housing 10 to the outside of the housing 10. The light source 33 is preferably powered by the energy storage unit 24 and controlled by the control unit 26.

The linearly polarized light sensor 36 detects linearly polarized light and converts the received/detected light into an electrical output. The linearly polarized light sensor 36 outputs an electrical signal based on the detected light, in particular the amount or intensity of detected light. The linearly polarized light sensor 36 may comprise one or more optical sensors 37 such as photodiodes. The optical sensor 37 may detect only light having a specific wavelength, or a range of wavelengths. The optical sensor 37 may be variable. That is, the specific wavelength or range of wavelengths detected by the optical sensor 37 may be variable. This wavelength(s) detected by such an optical sensor 37 may be selected by changing a voltage applied to the optical sensor 37.

The linearly polarized light sensor 36 is configured to detect linearly polarized light returned from the linearly polarized light source via the outside of the housing, such as through the light transmissive part 12 of the housing 10, and output an electrical signal based on the detected linearly polarized light. In other words, the linearly polarized light sensor 36 is configured to detect light that has been emitted by the linearly polarized light source 32 from inside the housing 10 to the outside of the housing 10 via the light transmissive part 12 of the housing 10, and that has returned to the inside of the housing 10 via the light transmissive part 12.

The returned light may have travelled from the linearly polarized light source 32 through the light transmissive part 12 to a region outside the housing 10, before returning back through the light transmissive part 12 to the inside of the housing 10, where it is detected by the linearly polarized light sensor 36.

The wireless communication module 20 is configured to wirelessly transmit a signal based on the electrical signal output by the linearly polarized light sensor 36 to the external wireless communication device 2. In other words, the wireless communication module 20 is configured to wirelessly transmit a signal that is a function of the light detected by the linearly polarized light sensor 36, whether this be a function of the intensity of the light, optical rotation of the light, or amount of refraction of the light. As such, the signal is also a function of the concentration of glucose in the body fluid in the vicinity of the implantable device 1.

The wireless signal transmitted by the wireless communication module 20 to the external wireless communication device 2 can be processed by the external wireless communication device 2, or a different apparatus, to provide an output which is dependent upon the glucose concentration of the body fluid being measured by the implantable device 1, such as a value of glucose concentration. The implantable device 1 may be calibrated by first performing a standard blood glucose test using a lancet.

In some embodiments, the implantable device 1 further comprises a temperature sensor 39, as shown in FIG. 2. The temperature sensor 39 is preferably located adjacent to or in the vicinity of the glucose measurement unit 30, but may be located anywhere within the implantable device 1 where it is desired to measure a temperature. The wireless communication module 20 may be configured to wirelessly transmit a signal based on a temperature measured by the temperature sensor 39 to the external wireless communication device 2. This signal may be a part of the aforementioned wireless signal based on the electrical signal output by the linearly polarized light sensor 36, or may be a separate signal.

Some of the measurements and operations performed by the glucose measurement unit 30 as described herein are temperature dependent. By providing a temperature sensor 39 and taking a temperature measurement, the temperature in the vicinity of the implantable device 1 can be taken into account when processing or interpreting measurements made by the implantable device 1. The temperature sensor 39 is, however, optional, since a temperature could be measured using a device not forming part of the implantable device 1, or else a temperature could be approximated (for example it could be assumed that the temperature inside a human body is 37° C.).

According to some aspects of the present disclosure, optical rotation of linearly polarized light passing through a body fluid can be directly or indirectly determined by the implantable device 1. By providing an output based upon the angle of rotation of linearly polarized light passing through the fluid, a value for the concentration of glucose in a body fluid can be determined. The output is provided using the linearly polarized light source 32 configured to emit linearly polarized light to outside the housing 10 of the implantable device 1, and the linearly polarized light sensor 36 configured to detect light returned from the linearly polarized light source 32 via the outside of the housing 10, wherein the output is an electrical signal based on the detected linearly polarized light, in particular the intensity of the detected light.

Glucose is an optically active material. That is, the plane of polarization of linearly polarized light is rotated as the light travels through a glucose solution. For a solution of glucose, the rotation angle α of the plane of polarization of the linearly polarized light is dependent upon the concentration p of glucose in the solution, the path length L of the light through the solution, the wavelength A of the light, and the temperature T of the glucose solution.

Specific rotation $[\alpha]^T_\lambda$ is an intrinsic property of a compound in a solution and is the angle of rotation of the plane of polarization of a ray of monochromatic light that passes through a sample of a compound in a solution, per unit distance-concentration product.

Specific rotation is dependent upon temperature of the solution and wavelength of the polarized light. The concentration of glucose in a solution can be determined by measuring the angle α through which the plane of polarization of linearly polarized light is rotated as it travels through the solution, and the path length L of the linearly polarized light through the solution. If the temperature T of the solution and the wavelength A of the linearly polarised light are known or approximated, then a value for the specific rotation of glucose can be looked-up for that temperature and wavelength. The concentration of glucose in the solution can then be determined from the angle α, specific rotation $[\alpha]^T_\lambda$, and path length L according to the following equation:

$$[\alpha]^T_\lambda = \frac{\alpha}{\beta \cdot L}$$

It can be approximated that a significant amount of the optical rotation of linearly polarised light through a body fluid such as blood or interstitial fluid is caused by glucose rather than other components of the body fluid. The optical activity of other components in the body fluid can therefore generally be disregarded. Therefore by determining the angle of rotation of linearly polarized light passing through body fluid, a good approximation of the glucose concentration within the body fluid can be determined. Determination of the glucose concentration within the body fluid can be carried out by the implantable device 1, for example by the control unit 26, or by the external wireless communication device 2.

Determining the glucose concentration may comprise processing the electrical signal output by the linearly polarized light sensor 36 or the signal based on the electrical signal that is wirelessly transmitted to the external wireless communication device 2, to determine a measurement value. A glucose concentration value may be determined by comparing the measurement value to a look-up table comprising a plurality of measurement values and their corresponding glucose concentration values.

As discussed previously, when the implantable device 1 is implanted, body fluid will contact an outer surface 11 of the housing 10, preferably light transmissive part 12. Light from the linearly polarized light source 32 passes through light transmissive part 12 to outside the housing 10 and is optically rotated as it passes through body fluid outside the housing 10. That is, the plane of polarization of the light is rotated through an angle as it passes through the body fluid.

At least part of the light that has been optically rotated by the body fluid returns through the light transmissive part 12 towards the inside of the housing 10 and is detected by linearly polarized light sensor 36. The linearly polarized light sensor 36 detects light of a particular linear polarization and outputs an electrical signal based on the amount of detected linearly polarized light. The plane of polarization of the linearly polarized light emitted by the linearly polarized light source 32 is rotated by the glucose in the body fluid. The amount of rotation is dependent upon the glucose concentration within the body fluid. The amount of light detected by the linearly polarized light sensor 36 will therefore be a function of the glucose concentration within the body fluid. The linearly polarized light sensor 36 is configured to output an electrical signal based on the detected linearly polarized light. The electrical signal will be a function of the amount of rotation of the plane of polarization of the light by the body fluid, and hence a function of the glucose concentration in the body fluid.

The electrical signal output by the linearly polarized light sensor 36 may be processed within the implantable device 1, for example by control unit 26. The wireless communication module 20 receives the electrical signal from the linearly polarized light sensor 36 and wirelessly transmits a signal based on the electrical signal to the external wireless communication device 2. In other words, the wirelessly transmitted signal is a function of the electrical signal, which is a function of the glucose concentration in the body fluid.

The signal transmitted by the wireless communication module 20 to the external wireless communication device 2 may be further processed by a processor (not shown) of the external wireless communication device 2 to provide a glucose concentration value for the body fluid.

Figure 3:
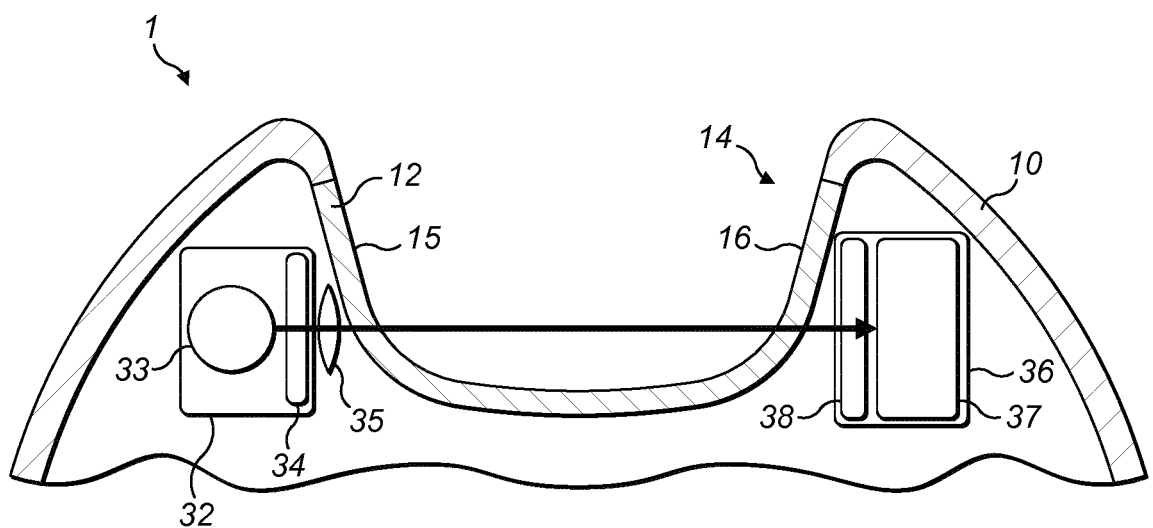
FIG. 3 is a schematic cross-section of part of an implantable device according to embodiments of the present disclosure.

FIG. 3 shows a partial schematic cross-section of an implantable device 1, such as the implantable device shown in FIG. 1B, wherein the glucose measurement unit 30 is configured to measure the rotation angle α of linearly polarized light travelling through the body fluid.

Figure 6:
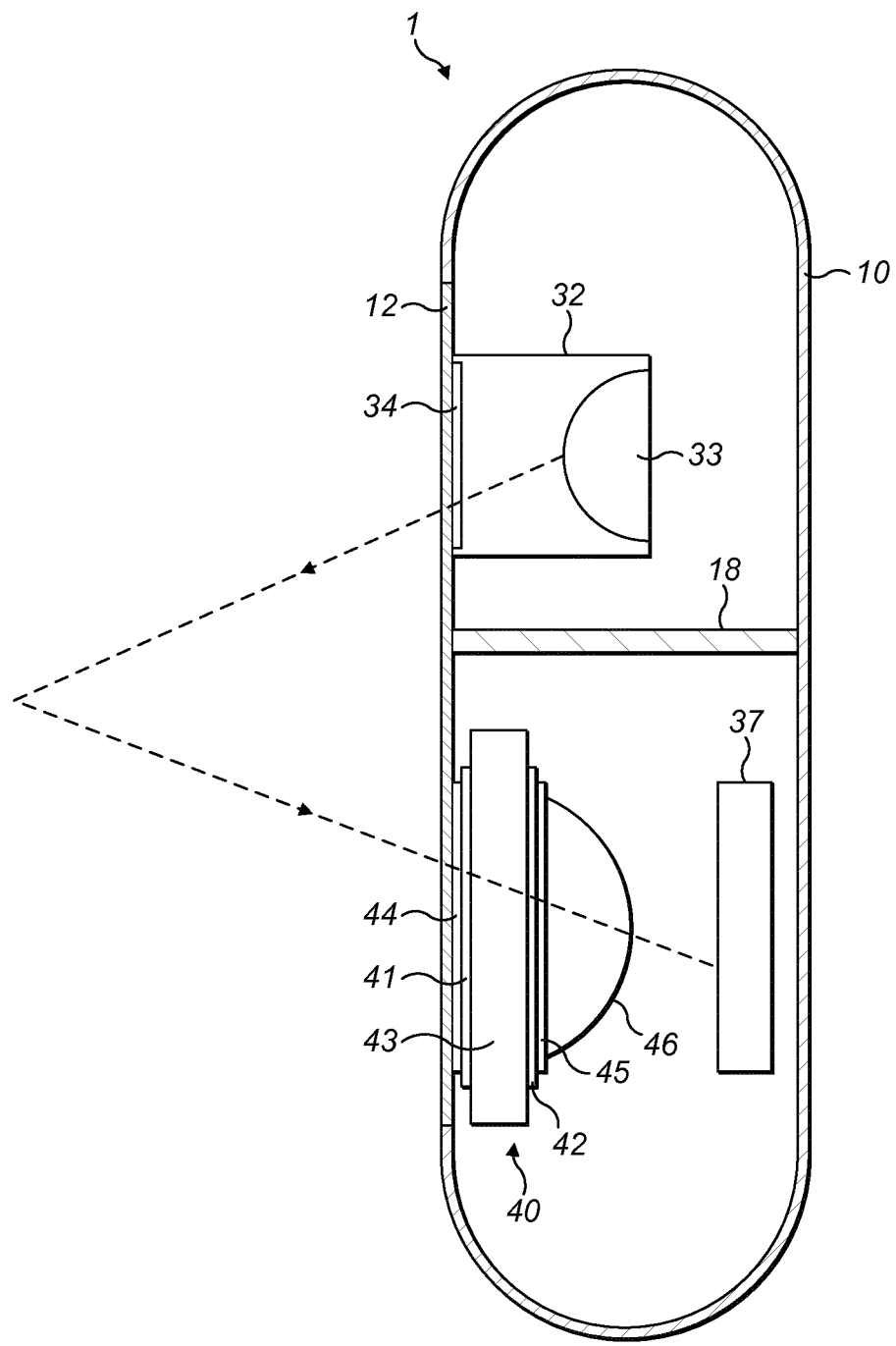
FIG. 6 is a schematic top-view cross-section of an implantable device according to embodiments of the present disclosure.

The implantable device 1 of FIG. 3 is shown to comprise groove 14, however in some examples groove 14 may not be present. As shown in FIG. 3, the first side wall 15 and second side wall 16 of the recess 14 each comprise at least part of the light transmissive part 12. The linearly polarized light source 32 may be arranged within the housing 10 such that the linearly polarized light emitted by the linearly polarized light source 32 to the outside of the housing 10 is emitted through the first side wall 15, via the light transmissive part 12, to a region outside the housing 10, before returning through the second side wall 16, via the light transmissive part 12, to be detected by linearly polarized light sensor 36, as indicated by the arrow in FIG. 3. In some examples the linearly polarized light source 32 and linearly polarized light sensor 36 may be arranged within the housing 10 such that the emitted light leaves and returns through the same surface of the light transmissive part 12, for example as illustrated in FIG. 6.

As shown in FIG. 3, linearly polarized light source 32 may comprise a light source 33 and linear polarizer 34. Light emitted from light source 33 may initially be emitted as unpolarised light (i.e. the light is polarised in a plurality of directions), before passing through linear polarizer 34, where the light is linearly polarized in a particular polarization plane. In other examples, no linear polarizer 34 is required because the emitted light is already linearly polarized. The linear polarizer 34 may be a linear polarizing filter, but other means of linearly polarizing the emitted light known in the art may be used.

The linearly polarized light is emitted via light transmissive part 12 to a region outside the housing 10. This region will be within body fluid when the implantable device is implanted.

In some embodiments the linear polarizer 34 is located within the housing 10, in an optical path between the light source 33 and light transmissive part 12 of housing 10, as shown in FIG. 3. In other embodiments the linear polarizer 34 is located outside the housing 10, coupled to an outer surface 11 of the housing 10, in an optical path between the light transmissive part 12 and linearly polarized light sensor 36. In other embodiments, the linear polarizer 34 is integrally formed with the housing 10.

As with any of the embodiments disclosed herein, the implantable device 1 may comprise at least one lens 35 arranged to focus light emitted from the linearly polarised light source 32. In particular, the lens 35 may focus the light emitted from the linearly polarised light source 32 towards a point outside the housing 10, and/or to focus light towards the linearly polarized light sensor 36.

FIG. 3 shows a lens 35 located within the housing 10, in an optical path between linearly polarized light source 32 and light transmissive part 12, however lens 35 may instead be located in any suitable location such as on a surface of the light transmissive part 12, on outer surface 11 of the housing 10. FIG. 3 also shows linear polarizer 34 located in an optical path between light source 33 and lens 35, however linear polarizer 34 may in some examples be located along the optical path after the lens 35.

Linearly polarized light emitted from the linearly polarized light source 32 to the outside of housing 10 and passing through the body fluid outside the housing 10 is optically rotated by the glucose within said body fluid so that the plane of polarization of the emitted light is rotated by an amount dependent upon the concentration of the glucose and the distance travelled by the light through the glucose. The distance travelled by the light through the glucose can be determined prior to implantation of the device, to be used for calculating a value of glucose concentration.

The linearly polarized light sensor 36 is arranged to detect linearly polarised light that has been emitted by the linearly polarized light source 32, passed through the body fluid, been optically rotated by the body fluid, and returned through the transmissive part 12 of the housing 10 from the region outside the housing 10. The linearly polarized light sensor 36 is further configured to output an electrical signal based on the detected linearly polarized, optically rotated light. The output is based on the rotation angle α of the linearly polarized light.

FIG. 3 shows the linearly polarized light sensor 36 comprises optical sensor 37 and a linearly polarized light filter 38. The linearly polarized light filter 38 is arranged to linearly polarize the light returned through the light transmissive part 12 of the housing 10 from the linearly polarized light source 32. In other words, the linearly polarized light filter 38 allows light with a particular linear polarization to pass through, while the remaining light is filtered out. Preferably, the linearly polarized light filter 38 is a linear polarization filter and allows light of a particular linear polarization to pass through or be transmitted. The optical sensor 37 is arranged to detect linearly polarised light emitted from the linearly polarized light source 32 via the outside of the housing 10 that has passed through the linearly polarized light filter 38, and outputs an electrical signal based on the detected light linearly polarized by the linearly polarized light filter 38.

As shown in FIG. 3, the linearly polarized light filter 38 is located in an optical path between the linearly polarized light source 32 and optical sensor 37, between the optical sensor 37 and the region outside the housing 10.

Preferably the plane of polarization of the linearly polarized light filter 38 is rotated with respect to the plane of polarization of the linearly polarized light emitted by the linearly polarized light source 32 about the optical path of the light, for example such that it is orthogonal to the plane of polarization of the linear polarizer 34. As such, the amount of linearly polarized light from the light source 33 and linear polarizer 34 detected by optical sensor 37 will be dependent upon the amount of optical rotation of the light. This optical rotation takes place as the linearly polarized light passes through the body fluid containing glucose. The amount of optical rotation, and therefore the amount of light detected by optical sensor 37 will depend upon the concentration of glucose in the body fluid. As such, the electrical signal output by the optical sensor 37 is based on the amount of optical rotation of the linearly polarized light and hence the concentration of glucose in the body fluid.

In some embodiments, a plane of polarization of the linearly polarized light filter 38 is adjustable relative to a plane of polarization of the linearly polarized light source 32. That is, an angle of the plane of polarization of the linearly polarized light filter 38 may be adjustable/variable. In other words, the orientation of the linear polarization vector of light allowed to pass through the linearly polarized light filter 38 may be adjustable. The plane of polarization may be adjusted by application of an appropriate electrical signal to the linearly polarized light filter 38, for example by control unit 26. By varying/adjusting the plane of polarization of the linearly polarized light filter 38, a peak value of light intensity detected by the optical sensor 37 may be found. This peak value will be indicative of the predominant angle of rotation experienced by the light emitted from the linearly polarized light source 32 due to optical rotation by the body fluid.

Figure 4:
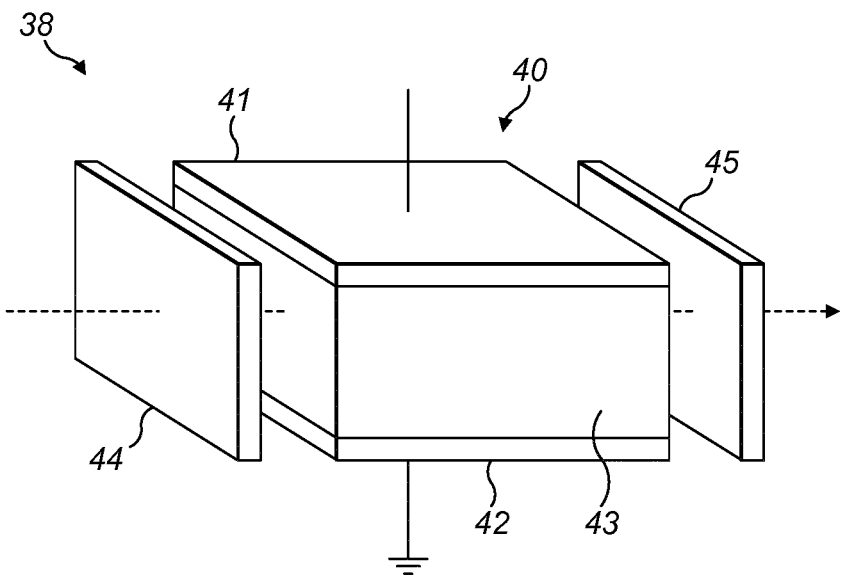
FIG. 4 is a schematic view of a Kerr cell for use in an implantable device according to embodiments of the present disclosure.

In some embodiments, the linearly polarized light filter 38 comprises a Kerr cell 40, as shown in FIG. 4. The Kerr cell 40 comprises a first electrode 41 and a second electrode 42. The first electrode 41 and second electrode 42 are separated a distance from each other. A potential difference can be applied between the first electrode 41 and second electrode 42, for example by control unit 26 and/or the glucose measurement unit 30. The potential difference generates an electric field between the first electrode 51 and second electrode 52.

A Kerr material 43 is located between the first electrode 41 and the second electrode 42. The Kerr material 43 is at least partially transparent to light such that light may pass through the Kerr material 43. The Kerr material 43 is preferably a Kerr liquid or Kerr crystal that can strongly exhibit the Kerr effect when an electric field passes through the Kerr material 43. The Kerr material 43 may be a Liquid Crystal Display (LCD) fluid, which has a large optical rotation, and so provides a good signal to noise ratio. In some embodiments the Kerr material 43 is permanently fixed between the first electrode 41 and second electrode 42. In other embodiments the Kerr material 43 comprises body fluid, which fills the space between the first electrode 41 and second electrode 42 once the implantable device 1 has been implanted, for example as later described with reference to FIGS. 9 and 10.

FIG. 4 shows the first electrode 41 and second electrode 42 as plate electrodes, although other forms of electrode may be used. The first electrode 41 and second electrode 42 may each be directly coupled to the Kerr material 43 such that a surface of the first electrode 41 is in contact with a surface of the Kerr material 43, while a surface of the second electrode 42 is in contact with another, opposing surface of the Kerr material 43. Alternatively, one or more of the first electrode 41 and second electrode 42 may be separated a distance from the Kerr material 43 such that they are not in direct contact with the Kerr material 43.

The linearly polarized light filter 38 of FIG. 4 further comprises a first linear polarizer 44 and a second linear polarizer 45, located on opposing sides of the Kerr cell 40. An exemplary path of light passing through the linearly polarized light filter 38 is indicated in FIG. 4 by the dotted line. Light, such as linearly polarized light returned from the linearly polarized light source 32 via the outside of the housing 10, first passes through first linear polarizer 44, which linearly polarizes the light. Preferably the plane of polarization of the first linear polarizer 44 is non-parallel to at least part of the electric field generated between the first electrode 41 and second electrode 42. Light linearly polarized by the first linear polarizer 44 then passes through the Kerr material 43 and through the electric field, before passing through a second linear polarizer 45, towards an optical sensor 37. Preferably the plane of polarization of the first linear polarizer 44 and second linear polarizer 45 are (substantially) orthogonal, that is, rotated 90° about the path of light travelling through the Kerr cell 40.

The plane of polarization of linearly polarized light that has passed through linear polarizer 44 and into Kerr cell 40 is rotated by the electric field generated between the first electrode 41 and second electrode 42. The amount of rotation is dependent upon the magnitude of the electric field. Changing the potential difference between the first electrode 41 and second electrode 42 changes the magnitude of the electric field, and therefore the amount of rotation of the linearly polarized light passing through the Kerr cell 40. As the amount of rotation changes, so too does the amount of light passing through linear polarizer 45 towards the optical sensor 37. By changing/varying the potential difference, the amount of light passing through the linearly polarized light filter 38 via the Kerr cell 40 changes. The Kerr cell 40 can therefore be used as a shutter.

The Kerr cell 40 can be used to determine the amount of optical rotation undertaken by linearly polarized light emitted by the linearly polarized light source 32 to outside the housing 10, wherein the amount of optical rotation is a function of glucose concentration within the body fluid.

The change in rotational angle φ of polarised light passing through the Kerr cell follows the function:

$$\varphi = 2\pi \cdot K \cdot L \frac{U^2}{d^2}$$

where K is the Kerr constant of the Kerr material 43, L is the path length of the light through the Kerr material 43, U is the potential difference between the first electrode 41 and second electrode 42, and d is the distance between the first electrode 41 and second electrode 42.

Figure 5:
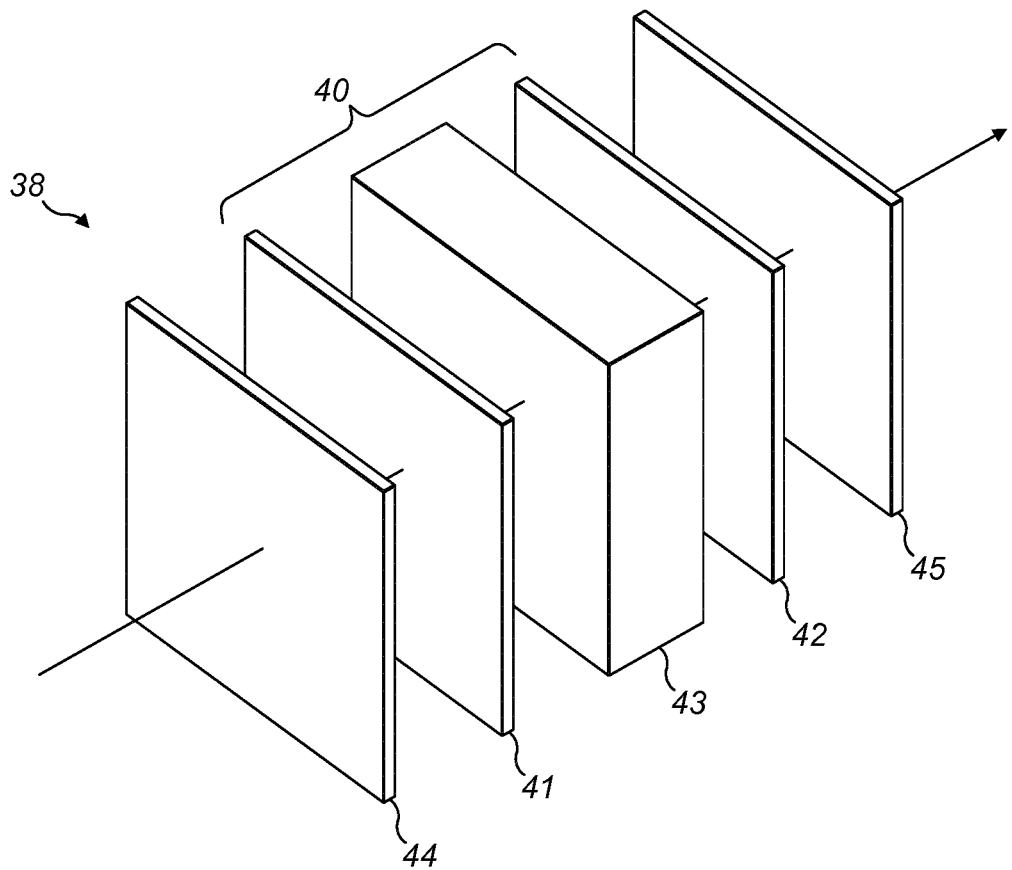
FIG. 5 is an exploded view of a compact Kerr cell for use in an implantable device according to embodiments of the present disclosure.

FIG. 5 shows an exploded view of an alternative construction of a linearly polarized light filter 38 comprising a Kerr cell 40 suitable for use in embodiments of the present disclosure. The linearly polarised light filter 38 of FIG. 5 is similar to the linearly polarised light filter 38 shown in FIG. 4, however the first electrode 41 is arranged in an optical path between the first linear polarizer 44 and the Kerr material 43, while the second electrode 42 is arranged in an optical path between the second linear polarizer 45 and the Kerr material 43.

An exemplary optical path of a beam of light is shown by the arrow in FIG. 5. Light returned from the linearly polarized light source 32 via outside the housing 10 first passes through the first linear polarizer 44, followed by the first electrode 41, followed by the Kerr material 43, followed by the second electrode 42, followed by the second linear polarizer 45. The path of the light may be substantially parallel to the electric field generated between the first electrode 41 and second electrode 42. In some examples the position of the first linear polarizer 44 and first electrode 41 may be swapped. In some examples the position of the second linear polarizer 45 and second electrode 42 may be swapped.

FIG. 6 shows an implantable device 1 according to some embodiments of the present disclosure, incorporating the linearly polarised light filter 38 and Kerr cell 40 shown in FIG. 5. Other configurations of the Kerr cell 40 and/or linearly polarised light filter 38 may be used, for example the linearly polarised light filter 38 of FIG. 4.

Linearly polarized light source 32, Kerr cell 40 and optical sensor 37 are arranged within housing 10 of implantable device 1. Linearly polarized light source 32 emits light to the outside of the housing 10 through light transmissive part 12. FIG. 6 shows linearly polarized light source 32 comprising light source 33 and linear polarizer 34, although linearly polarized light source 32 may alternatively not require a linear polarizer 34. Linear polarizer 34 and linear polarizer 44 are shown located inside the housing 10, but one or more of each may be located outside the housing 10.

An exemplary path taken by the linearly polarized light emitted by the linearly polarized light source 32 is shown by the dotted line in FIG. 6. The linearly polarized light is emitted to the outside of the housing 10. In use, when the implantable device 1 is implanted into a body, the linearly polarized light will be emitted into body fluid at least partially surrounding the implantable device 1. A portion of the linearly polarized light that has been emitted to the outside of the housing 10 by the linearly polarized light source 32 will be returned through the housing 10. This may be due to the portion of light being reflected by the body fluid. In some examples, the light returns through the housing 10 with the assistance of one or more lenses, or due to the shape of the implantable device 1, for example the provision of a recess 14. Various means by which light is returned are described throughout.

The linearly polarized light filter 38 is arranged within the housing 10 such that light returned from the linearly polarized light source 32 via outside the housing 10 passes through the first linear polarizer 44, followed by the Kerr cell 40, followed by the second linear polarizer 45 before being detected by the optical sensor 37.

The potential difference applied across the first electrode 41 and second electrode 42 may be varied over time. Consequently, the amount of light detected by the optical sensor 37, and the electrical signal output by the optical sensor 37, will vary over time. The electrical signal output by the optical sensor 37 will be a function of the amount of rotation the linearly polarized light emitted by the linearly polarized light source 32 undergoes as it passes through body fluid outside the housing 10. The electrical signal output by the optical sensor 37 can be processed to determine the concentration of glucose in the body fluid.

FIG. 6 shows a lens 46 arranged adjacent the Kerr cell 40 to focus light that has passed through the Kerr cell 40 towards the optical sensor 37. FIG. 6 also shows the implantable device 1 comprising a wall 18 arranged between the linearly polarized light source 32 and optical sensor 37, to prevent light emitted from the linearly polarized light source 32 travelling directly to the optical sensor 37 without first travelling outside the housing 10.

Figure 7:
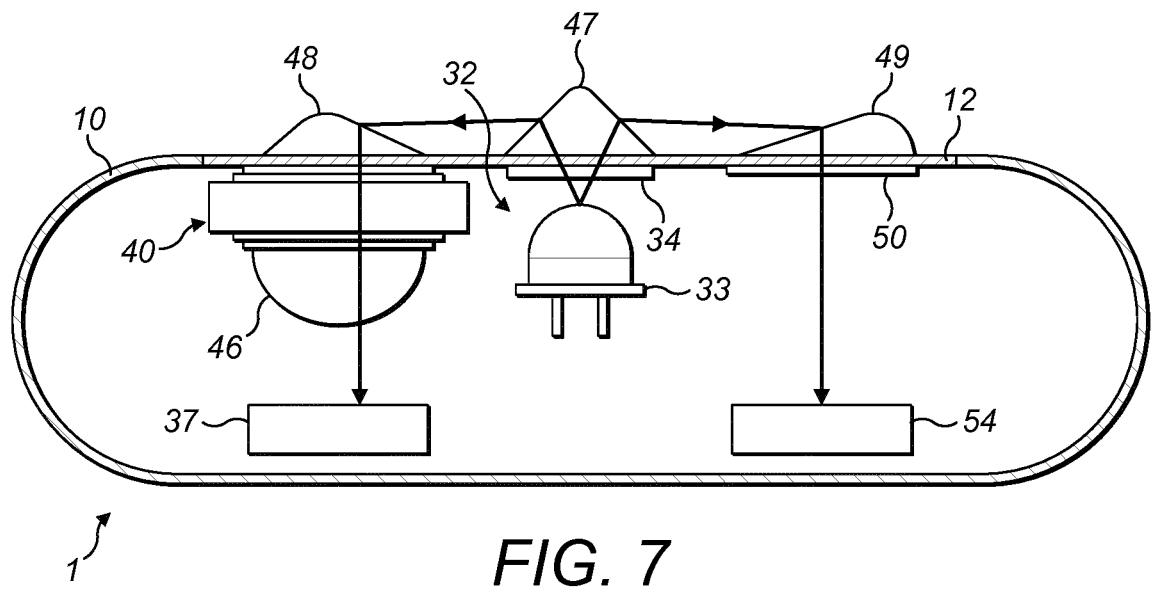
FIG. 7 is a schematic top-view cross-section of an implantable device according to embodiments of the present disclosure.

The implantable device 1 illustrated in FIG. 6 may be susceptible to interference, for example from the optical sensor 37 detecting light that does not originate from the linearly polarized light source 32, such as ambient light. FIG. 7 shows a partial schematic cross-section of an implantable device 1 similar to the implantable device 1 shown in FIG. 6, but configured for greater interference suppression.

Figure 8:
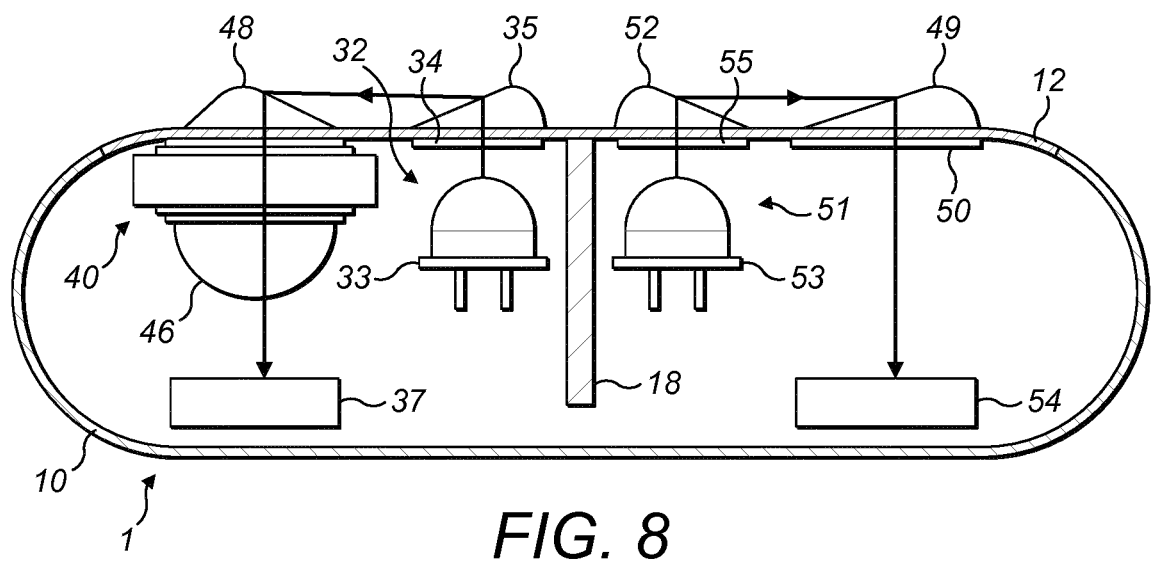
FIG. 8 is a schematic top-view cross-section of an implantable device according to embodiments of the present disclosure.

FIG. 7 and FIG. 8 show embodiments similar to FIG. 6, but with a reference channel comprising a second optical sensor 54.

Similar to the implantable device of FIG. 6, the implantable device 1 shown in FIG. 7 has a linearly polarized light source 32 comprising a light source 33 and linear polarizer 34, and a linearly polarized light filter 38 comprising a Kerr cell 40. However, here the glucose measurement unit 30 further comprises a second optical sensor 54 and an additional linear polarizer 50. The first optical sensor 37 and second optical sensor 54 may each comprise one or more photodiodes.

The linear polarizer 50 is arranged within housing 10 to linearly polarize at least part of the light returned from the linearly polarized light source 32 via the outside of the housing. The second optical sensor 54 is arranged to detect light linearly polarized by the linear polarizer 50, and output a second electrical signal based on the detected linearly polarized light.

Optional lens 47 can be arranged on the outer surface 11 of the housing 10 to focus the linearly polarized light emitted from the linearly polarized light source 32 to a point or region outside the housing 10, which would be in the body fluid when the implantable device 1 is implanted. FIG. 7 shows lens 47 focusing the linearly polarized light in two directions, a first direction towards the lens 48, wherein the lens 48 focusses light back to optical sensor 37, and a second direction towards the lens 49, wherein the lens 49 focusses light back towards optical sensor 54.

The first optical sensor 37 and second optical sensor 54 may be arranged to detect linearly polarized light originating from the linearly polarized light source 32 that has been reflected in the body fluid outside the housing 10, for example in the vicinity of the point or region outside the housing 10. The detected light may have been focused from the point or region outside the housing 10 towards the first optical sensor 37 and second optical sensor 54 by one or more lenses 46, 48, 49. Exemplary optical paths are illustrated in FIG. 7 by dotted lines.

The first optical sensor 37 and second optical sensor 54 are configured to each output an electrical signal, $S_{PDKerr}$ and $S_{PDRef}$ respectively, based on a detected intensity of linearly polarized light output from the linearly polarized light source 32 via outside the housing 10. The wireless communication module 20 is configured to wirelessly transmit a signal based on the electrical signal output by the first optical sensor 37 and the electrical signal output by the second optical sensor 54. Each electrical signal is a function of the angle through which the linear plane of polarization of light emitted by the linearly polarized light source 32 has been optically rotated, and is therefore a function of glucose concentration within the body fluid.

Linearly polarized light is emitted from the linear polarized light source 32. The potential difference applied between the first electrode 41 and second electrode 42 of the Kerr cell 40 is varied over time, for example increased over a period of time, until a maximum value of $SP_{DKerr}$ is determined, $maxS_{PDKerr}$. $S_{PDRef}$ is also determined, and remains constant with the varying potential difference. If $maxS_{PDKerr}=SPD_Ref$, then the potential difference $U_{Kerr}$ applied between the first electrode 41 and second electrode 42 to provide $maxS_{PDKerr}$ will be proportional to the concentration of glucose in the body fluid. The concentration of glucose C can therefore be found using the equation:

$$C = J \cdot U_{Kerr}$$

By finding the condition $maxS_{PDKerr}=S_{PDRef}$ and the fix factor J, the concentration of glucose C can be determined.

The device can be calibrated by in vitro testing, under laboratory conditions. Processing the electrical signal output by the optical sensor 37, and optical sensor 54 where appropriate, as well as the potential difference $U_{Kerr}$, to determine a glucose concentration can be done in accordance with means and techniques known in the art.

Providing the additional second optical sensor 54 and linear polarizer 50 as a reference channel allows the electrical signals output by the first optical sensor 37 and second optical sensor 54 to be processed (for example by the control unit 26 or external device 2) to reduce or remove the effects of interference or background noise. Such interference or background noise may, for example, be caused by ambient light or electrical noise in electrical components of the implantable device 1. As such, a more accurate determination of glucose concentration can be carried out. That is:

$$\frac{S_{PDKerr}}{S_{PDRef}}$$

is independent to ambient light, blood colouring due to meals ingested by the human or animal, and ambient temperature.

FIG. 8 shows a further embodiment similar to FIG. 7, however here the glucose measurement unit 30 further comprises a second linearly polarized light source 51, emits linearly polarized light for detection by the second optical sensor 54. FIG. 8 shows the second linearly polarized light source 51 comprising a second light source 53 and linear polarizer 55, wherein the first light source 33 and second light source 53 are optically isolated by a wall 18.

The second linearly polarized light source 51 is configured to emit linearly polarized light to the outside of the housing 10. Optional lens 52 focusses linearly polarized light emitted by the second linearly polarized light source 51 to a point or region outside the housing 10. Linear polarizer 50 is arranged to linearly polarize light returned from the second linearly polarized light source 51 via the outside of the housing 10. The second optical sensor 54 is arranged to detect the light linearly polarized by the linear polarizer 51 and output an electrical signal based on the detected light linearly polarized by the linear polarizer 51. The wireless communication module 20 is configured to wirelessly transmit a signal based on the second electrical signal output by the second optical sensor 54.

As described with reference to FIG. 7, the embodiment shown in FIG. 8 allows the electrical signals output by the first optical sensor 37 and second optical sensor 54 to be processed to reduce or remove the effects of interference or background noise.

Figure 9:
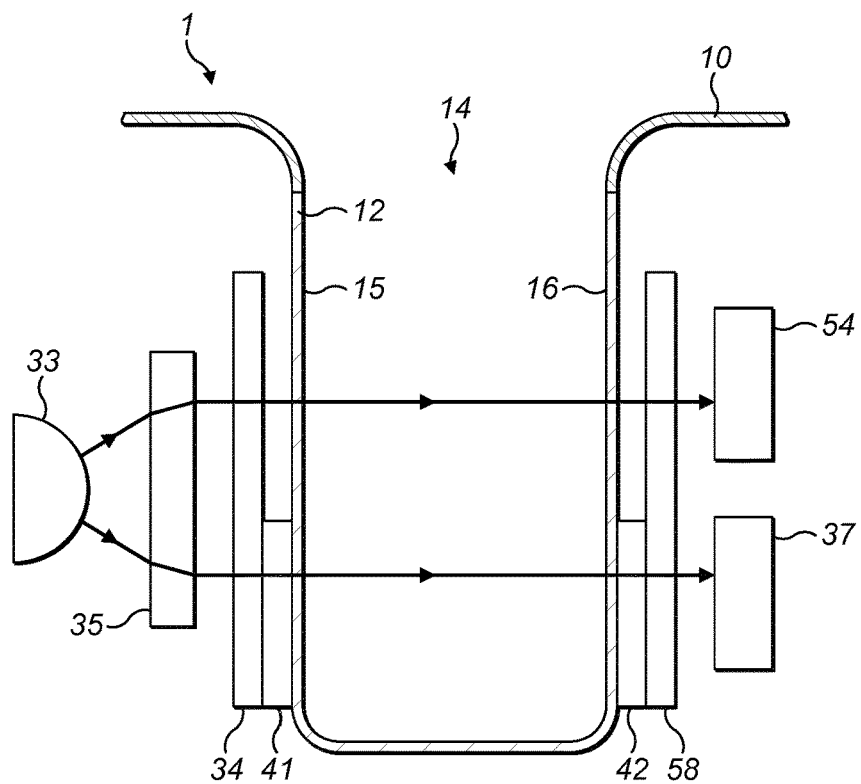
FIG. 9 is a schematic side-view cross-section of part of an implantable device according to embodiments of the present disclosure.

FIG. 9 shows an embodiment in which the housing 10 of the implantable device 1 comprises a recess 14 having a first side wall 15 and second side wall 16. The implantable device 1 of FIG. 9 has a Kerr cell 40 in which the first electrode 41 is located adjacent the first side wall 15 while the second electrode 42 is located adjacent the second side wall 16. Once the implantable device 1 is implanted, body fluid at least partially fills the recess 14 and acts as the Kerr material 43. A potential difference may be applied between the first electrode 41 and second electrode 42 as described previously, to generate an electric field between the first electrode 41 and second electrode 42, through the recess 14, and hence through part of the body fluid.

Light emitted by light source 33 is focused by lens 35 towards an outside of housing 10. The light emitted by light source 33 is linearly polarized by linear polarizer 34 before being emitted through the first side wall 15 to the outside of the housing 10. In the embodiment illustrated in FIG. 9, the outside is located within recess 14.

A first part of the linearly polarized light emitted from the light source 33 and linear polarizer 34 passes through first electrode 41 before reaching the outside of the housing 10. This first part of the linearly polarized light returns through the second side wall 16 to the inside of the housing 10, and through the second electrode 42, where it is then linearly polarized by linear polarizer 58, before being detected by first optical sensor 37, which outputs a first electrical signal as described previously. In other words, the first electrode 41, second electrode 42 and linear polarizer 58 are arranged such that a first part of the light linearly polarized by linear polarizer 34 that is detected by first optical sensor 37 passes through the first electrode 41, across the recess 14, before passing through the second electrode 42, followed by the linear polarizer 58, before being detected by first optical sensor 37. The first part of the linearly polarized light emitted from the light source 33 and linear polarizer 34 has therefore travelled through the electric field generated between the first electrode 41 and second electrode 42, when the potential difference is applied between the first electrode 41 and second electrode 42.

A second part of the linearly polarized light emitted from the light source 33 and linear polarizer 34 passes through first side wall 15 to outside the housing 10, before returning through second side wall 16 and linear polarizer 58, before finally being detected by second optical sensor 54, which outputs a second electrical signal as described previously. The second part of the linearly polarized light preferably does not pass through the first electrode 41 and/or second electrode 42, and therefore the second electrical signal output by the second optical sensor 54 can be used as a reference signal to reduce or remove the effects of interference or background noise, as discussed previously.

Figure 10:
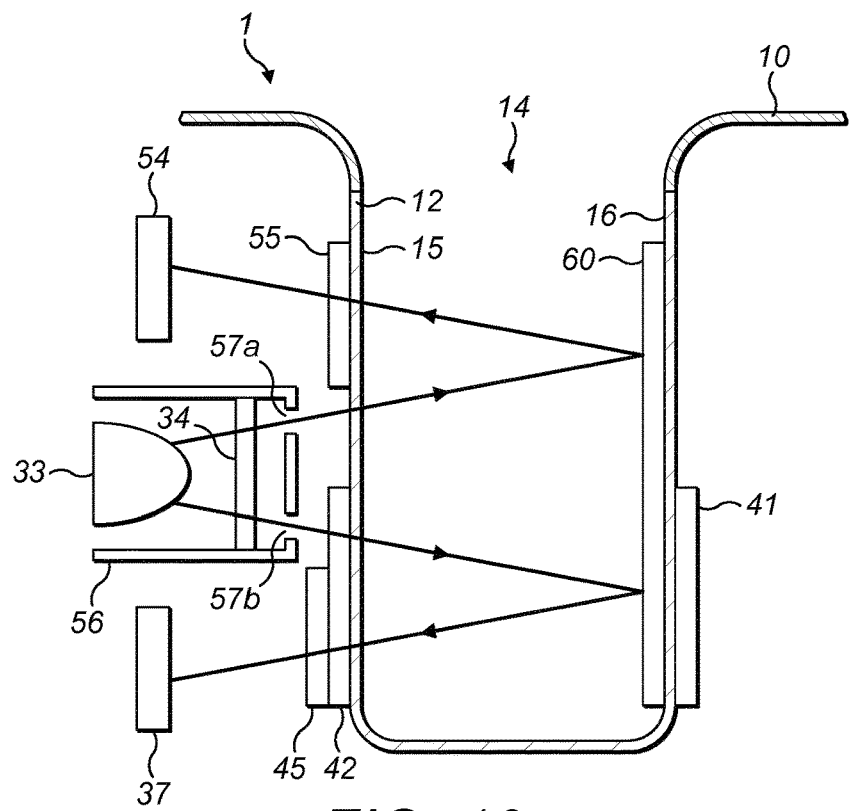
FIG. 10 is a schematic side-view cross-section of part of an implantable device according to embodiments of the present disclosure.

FIG. 10 shows an embodiment similar to that shown in FIG. 9, however the linearly polarized light emitted through the first side wall 15 is reflected by a mirror 60 located adjacent the second side wall 16. The reflected linearly polarized light returns through the first side wall 15 before part is detected by the first optical sensor 37 and part is detected by second optical sensor 54. The part of the returned light is that is detected by the second optical sensor 54 is linearly polarized by the linear polarizer 55 after it has returned through the first side wall 15. The part of the returned light is that is detected by the first optical sensor 37 is linearly polarized by the linear polarizer 45 after it has returned through the first side wall 15.

FIG. 10 shows an optional enclosure 56 at least partially surrounding the light source 33. The enclosure 56 comprises a first aperture 57a arranged to direct a first part of linearly polarized light emitted by the light source 33 and linear polarizer 34 towards a first region outside the housing 10, and a second aperture 57b arranged to direct a second part of linearly polarized light emitted by the light source 33 and linear polarizer 34 towards a second region outside the housing 10, different to the first region. The first part of the linearly polarized light is eventually detected by second optical sensor 54, while the second part of the linearly polarized light is eventually detected by first optical sensor 37.

In the embodiments shown in FIG. 9 and FIG. 10, a potential difference is applied between the first electrode 41 and second electrode 42 to generate an electric field through the body fluid in the recess 14. The potential difference may be varied over time, with the electrical signals output by the first optical sensor 37 and second optical sensor 54 being monitored over time and processed to determine the glucose concentration of body fluid within the recess 14, as discussed in relation to FIG. 7.

The embodiments illustrated by FIG. 9 and FIG. 10 may in some examples comprise a second linearly polarized light source 51 in a similar manner as described with reference to FIG. 8.

Figure 11:
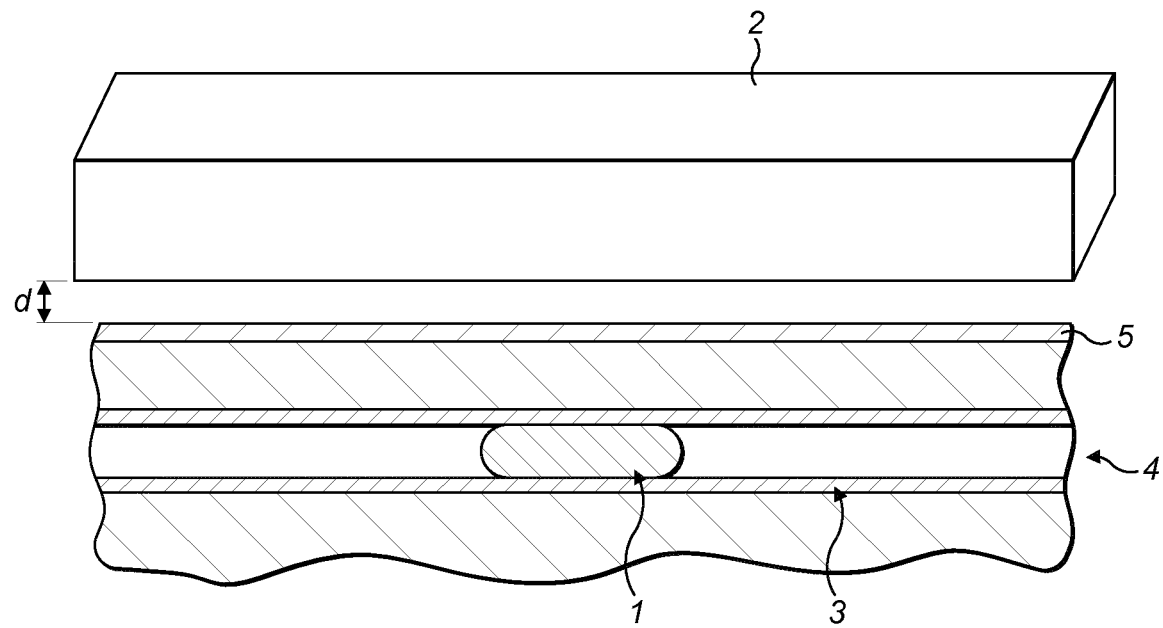
FIG. 11 is a schematic cross-section of a system comprising an implantable device and an external wireless communication device according to embodiments of the present disclosure, wherein the implantable device has been implanted into a blood vessel.

The present disclosure also relates to a system comprising an external wireless communication device 2 and an implantable device 1 according to any of the aforementioned embodiments. FIG. 11 shows such a system when the implantable device 1 has been implanted into a blood vessel 3 of a patient 4 (such as a human or animal).

In a similar manner to the wireless communication module 20 of the implantable device 1, the external wireless communication device 2 comprises an antenna, power supply and control unit (not shown). During use, the external wireless communication device 2 may be brought into close proximity of the implantable device 1. If the implantable device 1 has been implanted into a patient 4, this may involve bringing the external wireless communication device 2 into the vicinity of the skin 5 of the patient 4, for example within a distance d of less than around 2 cm from the skin 5.

The external wireless communication device 2 wirelessly transmits power to the implantable device 1 by electromagnetic induction between the antenna of the external wireless communication device 2 and the antenna 22 of the implantable device 1. A current is induced in the antenna 22 of the implantable device 1, providing power to any electrical circuitry within the device, such as the glucose measurement unit 30.

Responsive to receiving the power, or responsive to receiving an additional wireless signal transmitted by the external communication device 2 to the implantable device 1, the implantable device 1 proceeds with measuring the glucose concentration of body fluid in contact with the housing 10 of the implantable device 1. The linearly polarized light source 32 of the implantable device 1 emits linearly polarized light towards the light transmissive part 12 of the housing 10 of the implantable device 1. The linearly polarized light sensor 36 of the implantable device 1 detects linearly polarized light returned through the transmissive part 12, and outputs an electrical signal based on the detected light. The wireless communication module 20 of the implantable device 1 is configured to wirelessly transmit a signal based on the electrical signal to the external wireless communication device 2. The signal wirelessly transmitted to the external wireless communication device 2 by the implantable device 1 may be processed (for example by the external wireless communication device 2) to determine a value of glucose concentration for the body fluid.

The present disclosure also relates to a method of performing any of the aforementioned steps in relation to the implantable device 1 and external wireless communication device 2.

FIG. 12 shows a method according to embodiments of the present disclosure. At step 901, linearly polarized light is emitted by a linearly polarized light source 32 of an aforementioned implantable device 1 to outside a housing 10 of the implantable device 1. At step 902, a linearly polarized light sensor 36 of the implantable device 1 detects linearly polarized light returned from the first linearly polarized light source 32 via outside the housing 10. At step 903, an electrical signal based on the detected linearly polarized light is output by the linearly polarized light sensor 36. At step 904, a wireless communication module 20 of the implantable device 1 wirelessly transmits a signal based on the electrical signal to an external wireless communication device 1. As discussed previously, the signal wirelessly transmitted to the external wireless communication device 2 by the implantable device 1 may be processed (for example by the external wireless communication device 2) to determine a value of glucose concentration for the body fluid.

The terms "drug" or "medicament" are used synonymously herein and describe a pharmaceutical formulation containing one or more active pharmaceutical ingredients or pharmaceutically acceptable salts or solvates thereof, and optionally a pharmaceutically acceptable carrier. An active pharmaceutical ingredient ("API"), in the broadest terms, is a chemical structure that has a biological effect on humans or animals. In pharmacology, a drug or medicament is used in the treatment, cure, prevention, or diagnosis of disease or used to otherwise enhance physical or mental well-being. A drug or medicament may be used for a limited duration, or on a regular basis for chronic disorders.

As described below, a drug or medicament can include at least one API, or combinations thereof, in various types of formulations, for the treatment of one or more diseases. Examples of API may include small molecules having a molecular weight of 500 Da or less; polypeptides, peptides and proteins (e.g., hormones, growth factors, antibodies, antibody fragments, and enzymes); carbohydrates and polysaccharides; and nucleic acids, double or single stranded DNA (including naked and cDNA), RNA, antisense nucleic acids such as antisense DNA and RNA, small interfering RNA (siRNA), ribozymes, genes, and oligonucleotides. Nucleic acids may be incorporated into molecular delivery systems such as vectors, plasmids, or liposomes. Mixtures of one or more drugs are also contemplated.

The drug or medicament may be contained in a primary package or "drug container" adapted for use with a drug delivery device. The drug container may be, e.g., a cartridge, syringe, reservoir, or other solid or flexible vessel configured to provide a suitable chamber for storage (e.g., short- or long-term storage) of one or more drugs. For example, in some instances, the chamber may be designed to store a drug for at least one day (e.g., 1 to at least 30 days). In some instances, the chamber may be designed to store a drug for about 1 month to about 2 years. Storage may occur at room temperature (e.g., about 20° C.), or refrigerated temperatures (e.g., from about −4° C. to about 4° C.). In some instances, the drug container may be or may include a dual-chamber cartridge configured to store two or more components of the pharmaceutical formulation to-be-administered (e.g., an API and a diluent, or two different drugs) separately, one in each chamber. In such instances, the two chambers of the dual-chamber cartridge may be configured to allow mixing between the two or more components prior to and/or during dispensing into the human or animal body. For example, the two chambers may be configured such that they are in fluid communication with each other (e.g., by way of a conduit between the two chambers) and allow mixing of the two components when desired by a user prior to dispensing. Alternatively or in addition, the two chambers may be configured to allow mixing as the components are being dispensed into the human or animal body.

The drugs or medicaments contained in the drug delivery devices as described herein can be used for the treatment and/or prophylaxis of many different types of medical disorders. Examples of disorders include, e.g., diabetes mellitus or complications associated with diabetes mellitus such as diabetic retinopathy, thromboembolism disorders such as deep vein or pulmonary thromboembolism. Further examples of disorders are acute coronary syndrome (ACS), angina, myocardial infarction, cancer, macular degeneration, inflammation, hay fever, atherosclerosis and/or rheumatoid arthritis. Examples of APIs and drugs are those as described in handbooks such as Rote Liste 2014, for example, without limitation, main groups 12 (anti-diabetic drugs) or 86 (oncology drugs), and Merck Index, 15th edition.

Examples of APIs for the treatment and/or prophylaxis of type 1 or type 2 diabetes mellitus or complications associated with type 1 or type 2 diabetes mellitus include an insulin, e.g., human insulin, or a human insulin analogue or derivative, a glucagon-like peptide (GLP-1), GLP-1 analogues or GLP-1 receptor agonists, or an analogue or derivative thereof, a dipeptidyl peptidase-4 (DPP4) inhibitor, or a pharmaceutically acceptable salt or solvate thereof, or any mixture thereof. As used herein, the terms "analogue" and "derivative" refers to a polypeptide which has a molecular structure which formally can be derived from the structure of a naturally occurring peptide, for example that of human insulin, by deleting and/or exchanging at least one amino acid residue occurring in the naturally occurring peptide and/or by adding at least one amino acid residue. The added and/or exchanged amino acid residue can either be codable amino acid residues or other naturally occurring residues or purely synthetic amino acid residues. Insulin analogues are also referred to as "insulin receptor ligands". In particular, the term "derivative" refers to a polypeptide which has a molecular structure which formally can be derived from the structure of a naturally occurring peptide, for example that of human insulin, in which one or more organic substituent (e.g. a fatty acid) is bound to one or more of the amino acids.

Optionally, one or more amino acids occurring in the naturally occurring peptide may have been deleted and/or replaced by other amino acids, including non-codeable amino acids, or amino acids, including non-codeable, have been added to the naturally occurring peptide.

Examples of insulin analogues are Gly(A21), Arg(B31), Arg(B32) human insulin (insulin glargine); Lys(B3), Glu (B29) human insulin (insulin glulisine); Lys(B28), Pro(B29) human insulin (insulin lispro); Asp(B28) human insulin (insulin aspart); human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Examples of insulin derivatives are, for example, B29-N-myristoyl-des(B30) human insulin, Lys(B29) (N-tetradecanoyl)-des(B30) human insulin (insulin detemir, Levemir®); B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-gamma-glutamyl)-des(B30) human insulin, B29-N-omega-carboxypentadecanoyl-gamma-L-glutamyl-des(B30) human insulin (insulin degludec, Tresiba®); B29-N-(N-lithocholyl-gamma-glutamyl)-des(B30) human insulin; B29-N-(ω-carboxyheptadecanoyl)-des(B30) human insulin and B29-N-(ω-carboxyheptadecanoyl) human insulin.

Examples of GLP-1, GLP-1 analogues and GLP-1 receptor agonists are, for example, Lixisenatide (Lyxumia®), Exenatide (Exendin-4, Byetta®, Bydureon®, a 39 amino acid peptide which is produced by the salivary glands of the Gila monster), Liraglutide (Victoza®), Semaglutide, Taspoglutide, Albiglutide (Syncria®), Dulaglutide (Trulicity®), rExendin-4, CJC-1134-PC, PB-1023, TTP-054, Langlenatide/HM-11260C, CM-3, GLP-1 Eligen, ORMD-0901, NN-9924, NN-9926, NN-9927, Nodexen, Viador-GLP-1, CVX-096, ZYOG-1, ZYD-1, GSK-2374697, DA-3091, MAR-701, MAR709, ZP-2929, ZP-3022, TT-401, BHM-034. MOD-6030, CAM-2036, DA-15864, ARI-2651, ARI-2255, Exenatide-XTEN and Glucagon-Xten.

An examples of an oligonucleotide is, for example: mipomersen sodium (Kynamro®), a cholesterol-reducing antisense therapeutic for the treatment of familial hypercholesterolemia.

Examples of DPP4 inhibitors are Vildagliptin, Sitagliptin, Denagliptin, Saxagliptin, Berberine.

Examples of hormones include hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, and Goserelin.

Examples of polysaccharides include a glucosaminoglycane, a hyaluronic acid, a heparin, a low molecular weight heparin or an ultra-low molecular weight heparin or a derivative thereof, or a sulphated polysaccharide, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium. An example of a hyaluronic acid derivative is Hylan G-F 20 (Synvisc®), a sodium hyaluronate.

The term "antibody", as used herein, refers to an immunoglobulin molecule or an antigen-binding portion thereof. Examples of antigen-binding portions of immunoglobulin molecules include F(ab) and F(ab')2 fragments, which retain the ability to bind antigen. The antibody can be polyclonal, monoclonal, recombinant, chimeric, de-immunized or humanized, fully human, non-human, (e.g., murine), or single chain antibody. In some embodiments, the antibody has effector function and can fix complement. In some embodiments, the antibody has reduced or no ability to bind an Fc receptor. For example, the antibody can be an isotype or subtype, an antibody fragment or mutant, which does not support binding to an Fc receptor, e.g., it has a mutagenized or deleted Fc receptor binding region. The term antibody also includes an antigen-binding molecule based on tetravalent bispecific tandem immunoglobulins (TBTI) and/or a dual variable region antibody-like binding protein having cross-over binding region orientation (CODV).

The terms "fragment" or "antibody fragment" refer to a polypeptide derived from an antibody polypeptide molecule (e.g., an antibody heavy and/or light chain polypeptide) that does not comprise a full-length antibody polypeptide, but that still comprises at least a portion of a full-length antibody polypeptide that is capable of binding to an antigen. Antibody fragments can comprise a cleaved portion of a full length antibody polypeptide, although the term is not limited to such cleaved fragments. Antibody fragments that are useful in the present disclosure include, for example, Fab fragments, F(ab')2 fragments, scFv (single-chain Fv) fragments, linear antibodies, monospecific or multispecific antibody fragments such as bispecific, trispecific, tetraspecific and multispecific antibodies (e.g., diabodies, triabodies, tetrabodies), monovalent or multivalent antibody fragments such as bivalent, trivalent, tetravalent and multivalent antibodies, minibodies, chelating recombinant antibodies, tribodies or bibodies, intrabodies, nanobodies, small modular immunopharmaceuticals (SMIP), binding-domain immunoglobulin fusion proteins, camelized antibodies, and VHH containing antibodies. Additional examples of antigen-binding antibody fragments are known in the art.

The terms "Complementarity-determining region" or "CDR" refer to short polypeptide sequences within the variable region of both heavy and light chain polypeptides that are primarily responsible for mediating specific antigen recognition. The term "framework region" refers to amino acid sequences within the variable region of both heavy and light chain polypeptides that are not CDR sequences, and are primarily responsible for maintaining correct positioning of the CDR sequences to permit antigen binding. Although the framework regions themselves typically do not directly participate in antigen binding, as is known in the art, certain residues within the framework regions of certain antibodies can directly participate in antigen binding or can affect the ability of one or more amino acids in CDRs to interact with antigen. Examples of antibodies are anti PCSK-9 mAb (e.g., Alirocumab), anti IL-6 mAb (e.g., Sarilumab), and anti IL-4 mAb (e.g., Dupilumab).

Pharmaceutically acceptable salts of any API described herein are also contemplated for use in a drug or medicament in a drug delivery device. Pharmaceutically acceptable salts are for example acid addition salts and basic salts.

Those of skill in the art will understand that modifications (additions and/or removals) of various components of the APIs, formulations, apparatuses, methods, systems and embodiments described herein may be made without departing from the full scope and spirit of the present disclosure, which encompass such modifications and any and all equivalents thereof.

Although claims have been formulated in this application to particular combinations of features, it should be understood that the scope of the disclosure also includes any novel features or any novel combinations of features disclosed herein either explicitly or implicitly or any generalization thereof, whether or not it relates to the same disclosure as presently claimed in any claim and whether or not it mitigates any or all of the same technical problems as does the present disclosure. The applicant hereby gives notice that new claims may be formulated to such features and/or combinations of features during the prosecution of the present application or of any further application derived therefrom.

Although several embodiments have been shown and described, it would be appreciated by those skilled in the art that changes may be made in these embodiments without departing from the principles of the disclosure, the scope of which is defined in the claims.

The invention claimed is:

1. An implantable device for measuring glucose concentration of a body fluid when implanted, the implantable device comprising:
   a housing;
   a glucose measurement unit contained in the housing, the glucose measurement unit comprising:
   a first linearly polarized light source configured to emit linearly polarized light to outside of the housing of the implantable device, and a linearly polarized light sensor configured to detect linearly polarized light returned from the first linearly polarized light source via the outside of the housing, and output a first electrical signal based on the detected linearly polarized light; and
   a wireless communication module contained in the housing, the wireless communication module configured to wirelessly communicate with an external wireless communication device, wherein the linearly polarized light sensor comprises a linearly polarized light filter and a first optical sensor, wherein the linearly polarized light filter is configured to linearly polarize the light returned through a light transmissive part of the housing from the first linearly polarized light source, and wherein the first optical sensor is configured to output the first electrical signal based on the detected light linearly polarized by the linearly polarized light filter, wherein the linearly polarized light filter comprises a Kerr cell arranged such that the linearly polarized light returned from the first linearly polarized light source via the outside of the housing passes through the Kerr cell before being detected by the first optical sensor, and
   wherein the glucose measurement unit further comprises a second optical sensor and a linear polarizer, wherein the linear polarizer is arranged to linearly polarize light returned via the outside of the housing from the first linearly polarized light source or from a second linearly polarized light source configured to emit linearly polarized light to the outside of the housing, wherein the second optical sensor is arranged to detect the light linearly polarized by the linear polarizer and output a second electrical signal based on the detected light linearly polarized by the linear polarizer, and wherein the wireless communication module is configured to wirelessly transmit a signal based on the first electrical signal and the second electrical signal to the external wireless communication device.

2. The implantable device according to claim 1, wherein a plane of polarization of the linearly polarized light filter is adjustable relative to a plane of polarization of the first linearly polarized light source.

3. The implantable device according to claim 1, wherein the Kerr cell comprises a first electrode and a second electrode, wherein the glucose measurement unit is configured to apply a potential difference between the first electrode and the second electrode to generate an electric field between the first electrode and second electrode, and wherein the linearly polarized light returned from the first linearly polarized light source via the outside of the housing passes through the first electrode and the second electrode, along a path substantially parallel to the electric field.

4. The implantable device according to claim 1, wherein the wireless communication module is configured to wirelessly receive power from the external wireless communication device.

5. The implantable device according to claim 1, wherein the implantable device is dimensioned to be implantable into a human blood vessel.

6. The implantable device according to claim 1, wherein the housing comprises a recess, wherein the light emitted by the first linearly polarized light source to the outside of the housing is emitted through a first side wall of the recess, and wherein the linearly polarized light detected by the linearly polarized light sensor is returned through a second side wall of the recess.

7. The implantable device according to claim 1, wherein the implantable device further comprises at least one lens arranged to focus the light emitted from the first linearly polarized light source towards a point outside the housing.

8. The implantable device according to claim 1, wherein the implantable device further comprises a temperature sensor, and wherein the wireless communication module is configured to wirelessly transmit a signal based on a temperature measured by the temperature sensor to the external wireless communication device.

9. A system comprising:
an implantable device comprising:
a housing; a glucose measurement unit contained in the housing, the glucose measurement unit comprising: a first linearly polarized light source configured to emit linearly polarized light to outside of the housing of the implantable device, and a linearly polarized light sensor configured to detect linearly polarized light returned from the first linearly polarized light source via the outside of the housing, and output a first electrical signal based on the detected linearly polarized light; and a wireless communication module contained in the housing, the wireless communication module configured to wirelessly communicate with an external wireless communication device, wherein the linearly polarized light sensor comprises a linearly polarized light filter and a first optical sensor, wherein the linearly polarized light filter is configured to linearly polarize the light returned through a light transmissive part of the housing from the first linearly polarized light source, and wherein the first optical sensor is configured to output the first electrical signal based on the detected light linearly polarized by the linearly polarized light filter, wherein the linearly polarized light filter comprises a Kerr cell arranged such that the linearly polarized light returned from the first linearly polarized light source via the outside of the housing passes through the Kerr cell before being detected by the first optical sensor; and wherein the glucose measurement unit further comprises a second optical sensor and a linear polarizer, wherein the linear polarizer is arranged to linearly polarize light returned via the outside of the housing from the first linearly polarized light source or from a second linearly polarized light source configured to emit linearly polarized light to the outside of the housing, wherein the second optical sensor is arranged to detect the light linearly polarized by the linear polarizer and output a second electrical signal based on the detected light linearly polarized by the linear polarizer; and
the external wireless communication device, wherein the wireless communication module of the implantable device is configured to wirelessly transmit a signal based on the first electrical signal and the second electrical signal to the external wireless communication device.

10. The system according to claim 9, wherein the external wireless communication device is a smartphone.

11. The system according to claim 9, wherein a plane of polarization of the linearly polarized light filter is adjustable relative to a plane of polarization of the first linearly polarized light source.

12. The system according to claim 9, wherein the Kerr cell comprises a first electrode and a second electrode, wherein the glucose measurement unit is configured to apply a potential difference between the first electrode and the second electrode to generate an electric field between the first electrode and second electrode, and wherein the linearly polarized light returned from the first linearly polarized light source via the outside of the housing passes through the first electrode and the second electrode, along a path substantially parallel to the electric field.

13. The system according to claim 9, wherein the wireless communication module is configured to wirelessly receive power from the external wireless communication device.

14. The system according to claim 9, wherein the implantable device is dimensioned to be implantable into a human blood vessel.

15. The system according to claim 9, wherein the housing comprises a recess, wherein the light emitted by the first linearly polarized light source to the outside of the housing is emitted through a first side wall of the recess, and wherein the linearly polarized light detected by the linearly polarized light sensor is returned through a second side wall of the recess.

16. A method comprising:
emitting linearly polarized light, by a first linearly polarized light source of a glucose measurement device of an implantable device, to outside of a housing of the implantable device;
detecting, by a linearly polarized light sensor of the glucose measurement device, linearly polarized light returned from the first linearly polarized light source via the outside of the housing;
outputting, by the linearly polarized light sensor of the glucose measurement device, a first electrical signal based on the detected linearly polarized light;
detecting, by a second optical sensor of the implantable device, light linearly polarized by a linear polarizer of the implantable device, wherein the linear polarizer is arranged to linearly polarize light returned via the outside of the housing from the first linearly polarized light source or from a second linearly polarized light source configured to emit linearly polarized light to the outside of the housing;
outputting, by the second optical sensor, a second electrical signal based on the detected light linearly polarized by the linear polarizer; and
wirelessly transmitting, by a wireless communication module of the implantable device, a signal based on the first electrical signal and the second electrical signal to an external wireless communication device.

* * * * *

UNITED STATES PATENT AND TRADEMARK OFFICE
CERTIFICATE OF CORRECTION

PATENT NO. : 11,517,224 B2
APPLICATION NO. : 16/765236
DATED : December 6, 2022
INVENTOR(S) : Klemm Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 269 days.

Signed and Sealed this
Twentieth Day of February, 2024

Katherine Kelly Vidal
*Director of the United States Patent and Trademark Office*